United States Patent
Jalgaonkar et al.

(10) Patent No.: US 12,350,417 B2
(45) Date of Patent: Jul. 8, 2025

(54) MEDICAL ASPIRATION

(71) Applicant: Covidien LP, Mansfield, MA (US)

(72) Inventors: Ujwal Jalgaonkar, Irvine, CA (US);
Gaurav Girdhar, Ladera Ranch, CA (US); Kamel M. Chair, Hayward, CA (US); Peter Skujins, Menifee, CA (US); David P. Marchesiello, Laguna Niguel, CA (US); Emma Hurst, Torrance, CA (US); Brad Jackson, San Diego, CA (US)

(73) Assignee: Covidien LP, Mansfield, MA (US)

( * ) Notice: Subject to any disclaimer, the term of this patent is extended or adjusted under 35 U.S.C. 154(b) by 858 days.

(21) Appl. No.: 16/748,376

(22) Filed: Jan. 21, 2020

(65) Prior Publication Data
US 2021/0220528 A1 Jul. 22, 2021

(51) Int. Cl.
*A61M 1/00* (2006.01)
*A61B 17/22* (2006.01)
*A61B 5/021* (2006.01)
*A61B 5/024* (2006.01)
*A61B 5/0245* (2006.01)
(Continued)

(52) U.S. Cl.
CPC .......... *A61M 1/743* (2021.05); *A61B 17/22* (2013.01); *A61B 5/021* (2013.01); *A61B 5/02416* (2013.01); *A61B 5/0245* (2013.01); *A61B 5/33* (2021.01); *A61B 2017/22079* (2013.01);
(Continued)

(58) Field of Classification Search
CPC ......... A61B 17/22; A61B 5/318; A61B 5/021; A61B 5/02416; A61B 5/0245; A61B 2017/22079; A61B 2217/005; A61B 5/02; A61M 25/00; A61M 2230/04; A61M 1/74; A61M 1/73; A61M 1/0023; A61M 1/1723; A61M 60/432; A61M 60/435; A61M 1/743
See application file for complete search history.

(56) References Cited

U.S. PATENT DOCUMENTS 3,955,574 A 5/1976 Rubinstein
6,458,323 B1 * 10/2002 Boekstegers ....... A61M 1/3621
604/4.01
(Continued)

FOREIGN PATENT DOCUMENTS

EP 1781366 B2 4/2015
WO 2009089390 A2 7/2009
(Continued)

OTHER PUBLICATIONS

International Search Report and Written Opinion of International Application No. PCT/US2021/012888, mailed May 18, 2021, 14 pp.
(Continued)

*Primary Examiner* — Rebecca E Eisenberg
*Assistant Examiner* — Rachel O'Connell
(74) *Attorney, Agent, or Firm* — Shumaker & Sieffert, P.A.

(57) ABSTRACT

In some examples, a medical aspiration system is configured to control medical aspiration based on a cardiac cycle of a patient. For example, a medical aspiration system can include a suction source configured to apply a suction force to a catheter to remove fluid from the catheter, and control circuitry configured to control the suction force applied by the suction source to the catheter based on a cardiac cycle of a patient.

24 Claims, 5 Drawing Sheets

(51) Int. Cl.
*A61B 5/33* (2021.01)
*A61M 25/00* (2006.01)

(52) U.S. Cl.
CPC ........ *A61B 2217/005* (2013.01); *A61M 25/00* (2013.01); *A61M 2230/04* (2013.01)

(56) References Cited

U.S. PATENT DOCUMENTS

| | | | |
|---|---|---|---|
| 7,223,253 B2* | 5/2007 | Hogendijk | A61M 1/81 604/9 |
| 10,335,260 B2 | 7/2019 | Janardhan et al. | |
| 10,531,883 B1 | 1/2020 | Deville et al. | |
| 11,096,712 B2 | 8/2021 | Teigen et al. | |
| 2010/0049134 A1* | 2/2010 | Schuman, Jr. | A61M 1/0023 417/474 |
| 2010/0298792 A1* | 11/2010 | Weston | A61M 1/732 604/319 |
| 2011/0263976 A1* | 10/2011 | Hassan | A61M 1/3613 604/523 |
| 2015/0306286 A1* | 10/2015 | Ross | A61M 1/743 604/319 |
| 2018/0064453 A1* | 3/2018 | Garrison | A61M 25/0067 |
| 2018/0250449 A1* | 9/2018 | Tjølsen | A61M 1/784 |
| 2018/0333525 A1* | 11/2018 | Medvedev | A61B 5/02438 |
| 2019/0008545 A1* | 1/2019 | Stulen | A61M 1/743 |

FOREIGN PATENT DOCUMENTS

| | | |
|---|---|---|
| WO | 2014151209 A1 | 9/2014 |
| WO | 2018019829 A1 | 2/2018 |

OTHER PUBLICATIONS

Communication pursuant to Article 94(3) EPC from counterpart European Application No. 21703572.4 dated Oct. 8, 2024, 7 pp.

* cited by examiner

MEDICAL ASPIRATION

TECHNICAL FIELD

This disclosure relates to a medical aspiration.

BACKGROUND

In some cases, medical aspiration can be used to remove material from a patient. For example, medical aspiration can be used to remove an occlusion from a blood vessel of a patient.

SUMMARY

This disclosure describes example medical devices and systems configured to control medical aspiration based on a cardiac cycle of a patient, and techniques for controlling aspiration based on the cardiac cycle. In examples described herein, an aspiration system is configured to control the amount of suction force applied to the aspiration catheter based on the cardiac cycle of a patient.

Clause 1: In some examples, a medical aspiration system comprises a suction source configured to apply a suction force to a catheter to remove fluid from the catheter; and control circuitry configured to control the suction force applied by the suction source to the catheter based on a cardiac cycle of a patient.

Clause 2: In some examples of the medical aspiration system of clause 1, the control circuitry is configured to control the suction force applied by the suction source based on the cardiac cycle by at least controlling the suction source to apply a first suction force during diastole and controlling the suction source to apply a second suction force during systole, the first suction force being different from the second suction force.

Clause 3: In some examples of the medical aspiration system of clause 2, the first suction force is greater than the second suction force.

Clause 4: In some examples of the medical aspiration system of clause 2, the first suction force is less than the second suction force.

Clause 5: In some examples of the medical aspiration system of clause 2, the second suction force is zero.

Clause 6: In some examples of the medical aspiration system of any of clauses 1-5, the control circuitry is configured to control the suction force applied by the suction source based on the cardiac cycle by at least controlling the suction source to generate a first suction force at a distal opening of a catheter during a first part of the cardiac cycle and to generate a second suction force at the distal opening of the catheter during a second part of the cardiac cycle different from the first part, the second suction force being greater than the first suction force.

Clause 7: In some examples of the medical aspiration system of clause 6, the second part of the cardiac cycle corresponds to diastole.

Clause 8: In some examples of the medical aspiration system of clause 6, the second part of the cardiac cycle corresponds to systole.

Clause 9: In some examples of the medical aspiration system of any of clauses 1-8, the system further comprises sensing circuitry configured to generate a signal indicative of the cardiac cycle of the patient, wherein the control circuitry is configured to receive the signal from the sensing circuitry and control the suction force applied to the catheter based on the signal.

Clause 10: In some examples of the medical aspiration system of clause 9, the signal comprises at least one of an electrocardiogram, an electrogram, a photoplethysmogram, or a blood pressure signal.

Clause 11: In some examples of the medical aspiration system of clause 9, the sensing circuitry comprises at least one of an electrocardiogram sensor, an electrogram sensor, a blood oxygen saturation sensor, or an arterial blood pressure sensor.

Clause 12: In some examples of the medical aspiration system of any of clauses 1-11, the system further comprises the catheter fluidically coupled to the suction source.

Clause 13: In some examples of the medical aspiration system of any of clauses 1-12, the suction source comprises an evacuation volume fluidically coupled to a pump, wherein the pump is configured to draw the fluid from the catheter into the evacuation volume Clause 14: In some examples of the medical aspiration system of clause 13, the evacuation volume comprises a discharge reservoir, the system further comprising: a fluid source reservoir comprising an incompressible fluid; and a valve movable between a first position and a second position, wherein in the first position, the valve fluidically couples the fluid source reservoir and the catheter and does not fluidically couple the suction source and the catheter, and wherein in the second position, the valve fluidically couples the suction source and the catheter and does not fluidically couple the fluid source reservoir and the catheter, wherein the control circuitry is configured to control the suction force applied by the suction source to the catheter based on the cardiac cycle by at least controlling movement of the valve between the first position and the second position based on the cardiac cycle.

Clause 15: In some examples of the medical aspiration system of any of clauses 1-14, the control circuitry is configured to control the suction force applied by the suction source to the catheter based on the cardiac cycle by at least cycling the suction source between an on-phase and an off-phase.

Clause 16: In some examples of the medical aspiration system of any of clauses 1-15, the control circuitry is configured to synchronize the application of suction force with the cardiac cycle.

Clause 17: In some examples of the medical aspiration system of any of clauses 1-16, the control circuitry is configured to synchronize the application of suction force with one portion of the cardiac cycle.

Clause 18: In some examples of the medical aspiration system of any of clauses 1-17, the control circuitry is configured to synchronize the application of suction force with one portion of the cardiac cycle, and the application of reduced suction force or no suction force with another portion of the cardiac cycle.

Clause 19: In some examples of the medical aspiration system of any of clauses 1-18, the control circuitry is configured to synchronize the application of suction force with one portion of the cardiac cycle, and apply reduced suction force or no suction force during the remainder of the cardiac cycle.

Clause 20: In some examples of the medical aspiration system of any of clauses 1-19, the suction source comprises a pulsator, and the control circuitry is configured to control the suction force applied by the suction source by controlling the pulsator.

Clause 21: In some examples of the medical aspiration system of clause 20, the pulsator comprises a valve.

Clause 22: In some examples of the medical aspiration system of clause 20, the pulsator is configured to fluidically connect and disconnect the suction source and the catheter.

Clause 23: In some examples of the medical aspiration system of any of clauses 1-22, the suction source comprises a pump.

Clause 24: In some examples of the medical aspiration system of any of clauses 1-23, the suction source comprises an evacuation volume.

Clause 25: In some examples of the medical aspiration system of clause 24, the evacuation volume comprises a canister.

Clause 26: In some examples of the medical aspiration system of any of clauses 1-25, a distal end of the catheter is configured to be advanced into a cerebral artery of the patient.

Clause 27: In some examples, a method comprises receiving, in a medical aspiration system, a signal indicative of a cardiac cycle of a patient; and controlling a suction force applied by a suction source of the medical aspiration system to a catheter to remove fluid from the catheter based on the signal indicative of the cardiac cycle.

Clause 28: In some examples of the method of clause 27, controlling the suction force applied by the suction source to the catheter comprises: controlling the suction source to apply a first suction force during diastole; and controlling the suction source to apply a second suction force during systole, the first suction force being different from the second suction force.

Clause 29: In some examples of the method of clause 28, the first suction force is greater than the second suction force.

Clause 30: In some examples of the method of clause 28, the first suction force is less than the second suction force.

Clause 31: In some examples of the method of clause 28, the second suction force is zero Clause 32: In some examples of the method of any of clauses 27-31, controlling the suction force applied by the suction source to the catheter comprises: controlling the suction source to generate a first suction force at a distal opening of the catheter during a first part of the cardiac cycle; and controlling the suction source to generate to generate a second suction force at the distal opening of the catheter during a second part of the cardiac cycle different from the first part, the second suction force being greater than the first suction force.

Clause 33: In some examples of the method of clause 32, the second part of the cardiac cycle corresponds to diastole or systole.

Clause 34: In some examples of the method of any of clauses 27-33, the signal comprises an electrocardiogram signal, a photoplethysmogram, or a blood pressure signal.

Clause 35: In some examples of the method of any of clauses 27-34, the method further comprises: sensing, by sensing circuitry, a physiological parameter indicative of cardiac cycle of the patient; and generating, by the sensing circuitry, the signal based on the sensed physiological parameter.

Clause 36: In some examples of the method of any of clauses 27-35, controlling the suction force created by the pump to the catheter comprises: controlling movement of a valve between a first position and a second position based on the cardiac cycle, wherein in the first position, the valve fluidically couples the catheter and a fluid source reservoir and does not fluidically couple the suction source and the catheter, and wherein in the second position, the valve fluidically couples the suction source and the catheter and does not fluidically couple the fluid source reservoir and the catheter.

Clause 37: In some examples of the method of any of clauses 27-36, controlling the suction force created by the suction source to the catheter comprises cycling the suction source between an on-phase and an off-phase.

Clause 38: In some examples of the method of any of clauses 27-37, controlling the suction force comprises synchronizing the application of suction force with the cardiac cycle.

Clause 39: In some examples of the method of any of clauses 27-38, controlling the suction force comprises synchronizing the application of suction force with one portion of the cardiac cycle.

Clause 40: In some examples of the method of any of clauses 27-39, controlling the suction force comprises synchronizing the application of suction force with one portion of the cardiac cycle, and the application of reduced suction force or no suction force with another portion of the cardiac cycle.

Clause 41: In some examples of the method of any of clauses 27-40, controlling the suction force comprises synchronizing the application of suction force with one portion of the cardiac cycle, wherein the method further comprises applying reduced suction force or no suction force during the remainder of the cardiac cycle.

Clause 42: In some examples of the method of any of clauses 27-41, the suction source comprises a pulsator, and controlling the suction force applied by the suction source comprises controlling the pulsator.

Clause 43: In some examples of the method of clause 42, the pulsator comprises a valve.

Clause 44: In some examples of the method of clause 42, the method further comprises, via the pulsator, fluidically connecting and disconnecting the suction source and the catheter.

Clause 45: In some examples of the method of any of clauses 27-44, the controlling is performed by control circuitry of the medical aspiration system.

Clause 46: In some examples of the method of clause 45, the receiving is performed by the control circuitry.

Clause 47: In some examples of the method of any of clauses 27-46, the method further comprises aspirating from a blood vessel of a patient via the catheter.

Clause 48: In some examples, a medical aspiration system comprises a suction source configured to apply a suction force to a catheter to remove fluid from the catheter; and control circuitry configured to receive a signal indicative of a cardiac cycle of a patient from sensing circuitry, determine a current part of the cardiac cycle of the patient based on the signal, and control the suction force applied by the suction source to the catheter based on the determined current part of the cardiac cycle.

Clause 49: In some examples of the medical aspiration system of clause 48, the control circuitry is configured to control the suction force applied by the suction source by at least: in response to determining the current part of the cardiac cycle is diastole, controlling the suction source to apply a first suction force, and in response to determining the current part of the cardiac cycle is systole, controlling the suction source to apply a second suction force during, the first suction force being different from the second suction force.

Clause 50: In some examples of the medical aspiration system of clause 49, the first suction force is greater than the second suction force.

Clause 51: In some examples of the medical aspiration system of clause 49, the first suction force is less than the second suction force.

Clause 52: In some examples of the medical aspiration system of clause 49, the second suction force is zero.

Clause 53: In some examples of the medical aspiration system of any of clauses 48-52, the control circuitry is configured to control the suction force applied by the suction source based on the determined current part of the cardiac cycle by at least controlling the suction source to generate a first suction force at a distal opening of a catheter during a first part of the cardiac cycle and to generate a second suction force at the distal opening of the catheter during a second part of the cardiac cycle different from the first part, the second suction force being greater than the first suction force.

Clause 54: In some examples of the medical aspiration system of clause 53, the second part of the cardiac cycle corresponds to diastole.

Clause 55: In some examples of the medical aspiration system of clause 53, the second part of the cardiac cycle corresponds to systole.

Clause 56: In some examples of the medical aspiration system of any of clauses 48-52, the system further comprises sensing circuitry configured to generate a signal indicative of the cardiac cycle of the patient, wherein the control circuitry is configured to receive the signal from the sensing circuitry and determine the current part of the cardiac cycle based on the signal.

Clause 57: In some examples of the medical aspiration system of clause 56, wherein the signal comprises at least one of an electrocardiogram, an electrogram, a photoplethysmogram, or a blood pressure signal.

Clause 58: In some examples of the medical aspiration system of clause 56, wherein the sensing circuitry comprises at least one of an electrocardiogram sensor, an electrogram sensor, a blood oxygen saturation sensor, or an arterial blood pressure sensor.

Clause 59: In some examples of the medical aspiration system of any of clauses 48-58, the system further comprises the catheter fluidically coupled to the suction source.

Clause 60: In some examples of the medical aspiration system of any of clauses 48-59, the suction source comprises an evacuation volume fluidically coupled to a pump, wherein the pump is configured to draw the fluid from the catheter into the evacuation volume.

Clause 61: In some examples of the medical aspiration system of clause 60, the evacuation volume comprises a discharge reservoir, the system further comprising: a fluid source reservoir comprising an incompressible fluid; and a valve movable between a first position and a second position, wherein in the first position, the valve fluidically couples the fluid source reservoir and the catheter and does not fluidically couple the suction source and the catheter, and wherein in the second position, the valve fluidically couples the suction source and the catheter and does not fluidically couple the fluid source reservoir and the catheter, wherein the control circuitry is configured to control the suction force applied by the suction source to the catheter based on the determined current part of the cardiac cycle at least controlling movement of the valve between the first position and the second position based on the cardiac cycle.

Clause 62: In some examples of the medical aspiration system of any of clauses 48-61, the control circuitry is configured to control the suction force applied by the suction source to the catheter based on the determined current part of the cardiac cycle by at least cycling the suction source between an on-phase and an off-phase.

Clause 63: In some examples of the medical aspiration system of any of clauses 48-62, the control circuitry is configured to synchronize the application of suction force with the cardiac cycle.

Clause 64: In some examples of the medical aspiration system of any of clauses 48-63, the control circuitry is configured to synchronize the application of suction force with one portion of the cardiac cycle.

Clause 65: In some examples of the medical aspiration system of any of clauses 48-64, the control circuitry is configured to synchronize the application of suction force with one portion of the cardiac cycle, and the application of reduced suction force or no suction force with another portion of the cardiac cycle.

Clause 66: In some examples of the medical aspiration system of any of clauses 48-65, the control circuitry is configured to synchronize the application of suction force with one portion of the cardiac cycle, and apply reduced suction force or no suction force during the remainder of the cardiac cycle.

Clause 67: In some examples of the medical aspiration system of any of clauses 48-66, the suction source comprises a pulsator, and the control circuitry is configured to control the suction force applied by the suction source by controlling the pulsator.

Clause 68: In some examples of the medical aspiration system of clause 67, the pulsator comprises a valve.

Clause 69: In some examples of the medical aspiration system of clause 67, the pulsator is configured to fluidically connect and disconnect the suction source and the catheter.

Clause 70: In some examples of the medical aspiration system of any of clauses 48-69, the suction source comprises a pump.

Clause 71: In some examples of the medical aspiration system of any of clauses 48-70, the suction source comprises an evacuation volume.

Clause 72: In some examples of the medical aspiration system of clause 71, the evacuation volume comprises a canister.

Clause 73: In some examples of the medical aspiration system of any of clauses 48-72, a distal end of the catheter is configured to be advanced into a cerebral artery of the patient.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
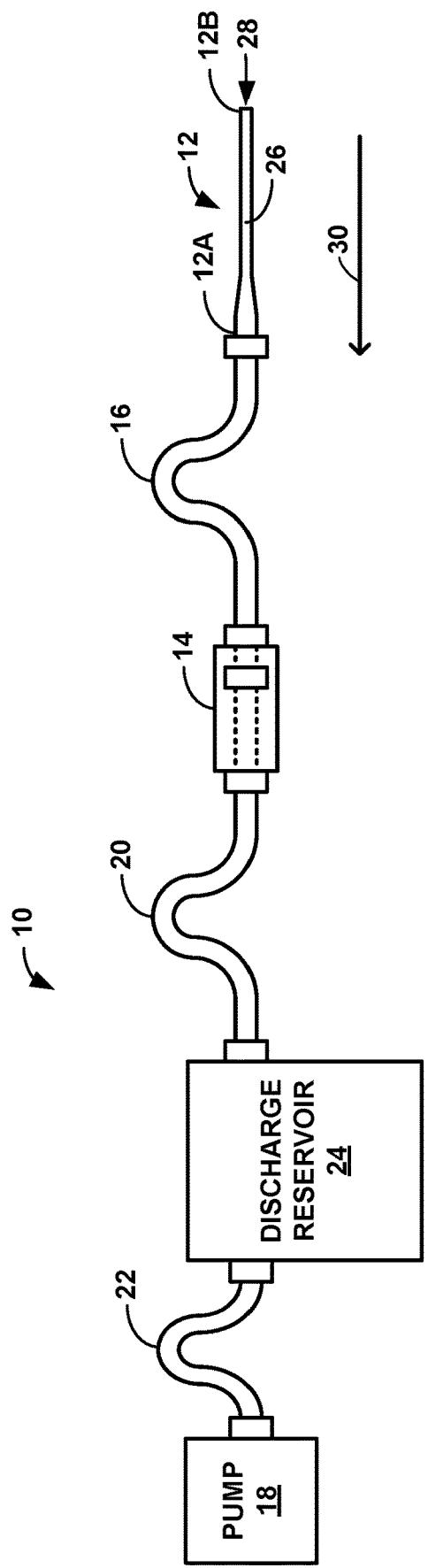
FIG. 1 is a schematic diagram illustrating an example aspiration system configured to control medical aspiration based on a cardiac cycle of a patient.

The disclosure describes medical aspiration systems configured to control medical aspiration based on a cardiac cycle of a patient, as well as medical devices and methods related to aspiration systems. A medical aspiration system may be used to treat a variety of conditions, including thrombosis. Thrombosis occurs when a thrombus (e.g., a blood clot or other embolus) forms and obstructs vasculature of a patient. To treat a patient with thrombosis, a clinician may position a medical catheter (also referred to herein as an aspiration catheter) in a blood vessel of the patient near the thrombus or other occlusion, and apply a suction force (also referred to herein as suction, suction force, or negative pressure) to the catheter (e.g., to one or more lumens of the catheter) to engage the thrombus with suction force at a tip of the catheter. Once the tip of the aspiration catheter has engaged the thrombus, the clinician may remove the aspiration catheter with the thrombus attached to the tip or suction off pieces of the thrombus (or the thrombus as a whole) until the thrombus is removed from the blood vessel of the patient through a lumen of the aspiration catheter itself and/or through the lumen of an outer catheter in which the aspiration catheter is at least partially positioned. The outer catheter can be, for example, a guide catheter configured to provide additional structural support to the aspiration catheter. The aspiration of the thrombus may be part of an aspiration procedure, such as, but not limited to, a medical procedure using A Direct Aspiration First Pass Technique (ADAPT) for acute stroke thrombectomy, or any other procedure for aspiration of thrombus or other material from the neurovasculature or other blood vessels. In addition, aspiration of thrombus can be performed concurrently with use of a thrombectomy device, such as a stent retriever, to facilitate removal of thrombus via mechanical thrombectomy as well as via aspiration.

In examples described herein, a medical aspiration system can be configured to control the amount of suction force applied to an aspiration catheter based on the cardiac cycle of a patient. For example, in some examples, control circuitry of the aspiration system is configured to determine which part of a cardiac cycle a heart of patient is in and control a suction source of the aspiration system to apply a first suction force during a first part of the cardiac cycle, such as diastole, and to control the suction source to apply a second suction force during a second part of the cardiac cycle, such as systole, where the first suction force is different from the second suction force. A part of a cardiac cycle can include a portion of the cardiac cycle and does not span multiple cardiac cycles. In some examples, the first suction force is greater than the second suction force, such that a greater suction force is applied to the aspiration catheter during the first part of the cardiac cycle. In other examples, the first suction force is less than the second suction force, such that a greater suction force is applied to the aspiration catheter during the second part of the cardiac cycle.

As used herein, "suction force" is intended to include within its scope related concepts such as suction pressure, vacuum force, vacuum pressure, negative pressure, fluid flow rate, and the like. A suction force can be generated by a vacuum, e.g. by creating a partial vacuum within a sealed volume fluidically connected to a catheter, or by direct displacement of liquid in a catheter or tubing via (e.g.) a peristaltic pump, or otherwise. Accordingly, suction forces or suction as specified herein can be measured, estimated, computed, etc. without need for direct sensing or measurement of force. A "higher," "greater" or "larger" (or "lower," "lesser" or "smaller") suction force described herein may refer to the absolute value of the negative pressure generated by the suction source on a catheter or another component, such as a discharge reservoir.

It is believed that controlling the amount of suction force applied to an aspiration catheter based on the cardiac cycle of a patient may more quickly and more effectively remove a thrombus from a blood vessel of a patient than applying a continuous or steady suction force.

A cardiac cycle includes different phases (also referred to as stages in some examples), and, in some examples, the control circuitry is configured to vary the suction force applied by the suction source to the aspiration system and/or catheter based on the current phase of the cardiac cycle of the patient. That is, in some examples, the aspiration system is configured to determine the current phase of the cardiac cycle of a patient and apply different amounts of suction force to the aspiration system and/or catheter during different phases of a cardiac cycle.

A cardiac cycle includes diastole, during which the heart muscles are relaxed and a heart chamber fills with blood, and systole, during which the heart muscles contract and pump blood out of the heart chamber. For example, in a patient with a healthy heart, atrial systole occurs during ventricular diastole to actively fill the ventricles during their diastole. In some examples, the phases of a cardiac cycle can include cardiac diastole, atrial systole, and ventricular systole. Atrial systole can be associated with a P-wave of a PQRST complex of an electrical cardiac signal, such as a cardiac electrogram (EGM) or electrocardiogram (ECG), and ventricular systole can be associated with a Q-deflection of the PQRST complex of the electrical cardiac signal. Systole referenced herein may refer to atrial systole or ventricular systole. In addition, diastole referenced herein may refer to atrial diastole or ventricular diastole.

In addition to or instead of these phases, the phases of a cardiac cycle can be described by the fluid flow in the heart. As an example, the phases of a cardiac cycle can be referred to as isovolumetric relaxation, ventricular filling, ventricular filling with atrial systole, isovolumetric contraction, and ejection.

In some cases, the control circuitry is configured to control the suction force applied by the suction source based on the cardiac cycle by at least controlling the suction source to generate a minimum (or decreased, or relatively lower) suction force at a distal end of a catheter during a first part of the cardiac cycle and to generate a maximum (or increased, or relatively higher) suction force at the distal end of the catheter during a second part of the cardiac cycle different from the first part. As an example, the second part can correspond to diastole, such as, but not limited to, the start of diastole, a mid-point of diastole, or an end of diastole. As another example, the second part of the cardiac cycle can correspond to systole, such as, but not limited to, the start of systole, a mid-point of systole, or an end of systole. As yet another example, the second part of the cardiac cycle can correspond to a maximum ejection phase of the cardiac cycle (e.g., as indicated by an M-wave of a PQRST complex of an electrical cardiac signal). Other manners of controlling the suction source based on the cardiac cycle of a patient can be used in other examples.

The control circuitry of an aspiration system can determine a cardiac cycle (e.g., the current phase of a cardiac cycle) using any suitable technique. For example, the control circuitry can determine a current phase of a cardiac cycle of a patient based on an electrical cardiac signal, a blood pressure, blood oxygen saturation, or another physiological parameter that changes as a function of a cardiac cycle of the patient. In some examples, an aspiration system includes or is otherwise communicatively coupled to sensing circuitry configured to generate a signal indicative of a physiological parameter of the patient indicative of the cardiac cycle, and the control circuitry is configured to receive the signal and determine the cardiac cycle (e.g., a specific phase of the cardiac cycle) based on the signal. The signal can include, for example, one or more of an ECG, an EGM, a photoplethysmogram (PPG), a heart sound phonocardiogram, or a blood pressure signal. The sensing circuitry can include, for example, one or more of an electrocardiogram sensor, an electrogram sensor, a blood oxygen saturation sensor, or an arterial blood pressure sensor.

In other examples, a device other than the control circuitry that controls the suction source determines the cardiac cycle of a patient and the control circuitry of the aspiration system receives information indicative of the cardiac cycle from the other device. The other device can include, for example, a heart monitor, a multiparametric monitor, or the like.

As is illustrated and described in further detail herein, the suction source can comprise a pump. A pump can comprise a direct-acting pump, which acts directly on a liquid to be displaced, or a tube containing the liquid. A direct-displacement pump can comprise a peristaltic pump, or a lobe, vane, gear, or piston pump, or other suitable pumps of this type. A pump can also comprise an indirect-acting pump, which acts indirectly on the liquid to be displaced. An indirect-acting pump can comprise a vacuum pump, which creates a partial vacuum in an evacuation volume fluidically coupled to the liquid to be displaced. The vacuum pump displaces a compressible fluid (e.g., a gas such as air) from the evacuation volume (e.g., a discharge reservoir, which can comprise a canister), generating suction force on the liquid. Accordingly, the evacuation volume (when present) can be considered part of the suction source The suction source can also comprise a pulsator. A pulsator can be employed to switch on, switch off, vary, oscillate, pulse, etc. the application of suction force from the suction source to the catheter or patient. Accordingly, the pulsator can fluidically couple or uncouple the catheter to or from the suction source as needed. The pulsator can comprise a valve, tubing clamp, tubing pincher, fluid switch, or the like, preferably configured for selective actuation as needed to fluidically couple or uncouple the catheter to or from the suction source in accordance with control of the aspiration system.

Control, operation, etc. of the suction source can comprise control, operation, etc. of any one or combination of the component(s) making up the suction source. Accordingly, where the suction source includes a pump, evacuation volume and pulsator, control of the suction source can comprise control of only the pump, of only the evacuation volume, or of only the pulsator, or of any combination of those components. Where the suction source includes only a pump, control of the suction source comprises control of the pump. Control of other suction sources may comprise control of only the pulsator, or of only the evacuation volume, or of only the pump, or of any combination of the components which are employed in the suction source.

FIG. 1 is a schematic diagram illustrating an example aspiration system 10 that includes a catheter 12, a fluid flow switch 14 coupled to catheter 12 through aspiration tubing 16, and a pump 18. Aspiration system 10 may be used in various medical procedures, such as a medical procedure to treat an ischemic insult, which may occur due to occlusion of a blood vessel (arterial or venous) that deprives brain tissue, heart tissue or other tissues of oxygen-carrying blood.

Aspiration system 10 is configured to remove fluid from catheter 12, e.g., draw fluid from catheter 12 into discharge reservoir 24, via a suction force applied by pump 18 to catheter 12 (e.g., to inner lumen 26 of catheter 12). For example, pump 18 can be configured to create a negative pressure within inner lumen 26 of catheter 12 to draw a fluid, such as blood, an aspiration fluid, more solid material, or a mixture thereof, in a direction indicated by arrow 30 and into inner lumen 26 via distal opening 28 of catheter 12. The negative pressure within inner lumen 26 can create a pressure differential between inner lumen 26 and the environment external to at least a distal portion of catheter 12 that causes fluid and other material to be introduced into inner lumen 26 via distal opening 28. For example, the fluid may flow from patient vasculature, into inner lumen 26 via distal opening 28, and subsequently through aspiration tubing 16, fluid flow switch 14, and aspiration tubing 20 into discharge reservoir 24. Accordingly, the suction source of aspiration system 10 of FIG. 1 comprises pump 18, an evacuation volume in the form of discharge reservoir 24, and a pulsator in the form of fluid flow switch 14.

In some examples, aspiration system 10 is also configured to deliver fluid from a fluid source (e.g., a fluid reservoir different from discharge reservoir 24) through inner lumen 26 of catheter 12 via a positive pressure applied by pump 18.

Catheter 12 and pump 18 can be fluidically coupled using any suitable configuration. In the example shown in FIG. 1, pump 18 is fluidically coupled to catheter 12 via aspiration tubing 22, discharge reservoir 24, aspiration tubing 20, fluid flow switch 14, and aspiration tubing 16. For example, pump 18 can be coupled to discharge reservoir 24 via aspiration tubing 22, and discharge reservoir 24 can be positioned between pump 18 and catheter 12. In these examples, pump 18 is configured to generate a partial vacuum in discharge reservoir 24 that causes fluid (e.g., blood) and more solid material (e.g., a thrombus) located within an inner lumen 26 of catheter 12 to be drawn into discharge reservoir 24 via tubing 16, 20 and fluid flow switch 14. In other examples, pump 18 can be more directly coupled to catheter 12 or may be further fluidically separated from catheter 12 by additional components.

Aspiration tubing 16, 20, 22, as well as other aspiration tubing described herein, is any suitable structure that defines a fluid pathway through which fluid and some relatively small fluid particles may flow between components of aspiration system 10. The tubing can be formed from any suitable material, such as, but not limited to, polymers, which can be reinforced with bonded, laminated or embedded tubular braids, coils, or other reinforcement member(s).

Catheter 12 is configured to be used as an aspiration catheter to remove a thrombus, such as a clot or other material such as plaques or foreign bodies, from vasculature of a patient. Catheter 12 defines at least one inner lumen, e.g., lumen 26 shown in FIG. 1, and at least one distal opening 28 that is open to lumen 26. Distal opening 28 may be at a distal-most end of catheter 12 and/or another position along catheter 12, such as in a sidewall of catheter 12 proximal to distal end 12B of catheter 12.

Catheter 12 includes an elongated body and a hub. The elongated body of catheter 12 is configured to be advanced through vasculature of a patient via a pushing force applied to a proximal portion of the elongated body. Catheter 12 includes any suitable construction for medical aspiration. In some examples, catheter 12 may include an inner liner, an outer jacket, and a structural support member, such as a coil and/or or a braid, positioned between at least a portion of the inner liner and at least a portion of the outer jacket. Catheter 12 may include other structures, such as an expandable member configured to radially expand within a vessel of a patient, e.g., to engage a clot within the vessel.

Catheter 12 is configured to be navigated to any suitable vascular site in a patient. In some examples, catheter 12 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. The elongated body of catheter 12 may be structurally configured to be relatively flexible, pushable, and relatively kink- and buckle-resistant, so that it may resist buckling when a pushing force is applied to a relatively proximal section of catheter 12 to advance the elongated body distally through vasculature, and so that it may resist kinking when traversing around a tight turn in the vasculature. In some examples, the elongated body is configured to substantially conform to the curvature of the vasculature. In addition, in some examples, the elongated body has a column strength and flexibility that enables at least the distal portion of the elongated body to be navigated from a femoral artery, through the aorta of the patient, and into the intracranial vascular system of the patient, e.g., to reach a relatively distal treatment site. Alternatively, the elongated body can have a column strength (and/or be otherwise configured) to enable the distal portion of the elongated body to be navigated from a radial artery via an access site in the arm, e.g. at or near the wrist, through the aorta of the patient or otherwise to a common carotid or vertebral artery, and into the intracranial vascular system of the patient, e.g., to reach a relatively distal treatment site.

Although primarily described as being used to reach relatively distal vasculature sites, catheter 12 may also be configured to be used with other target tissue sites. For example, catheter 12 may be used to access tissue sites throughout the coronary and peripheral vasculature, the gastrointestinal tract, the urethra, ureters, fallopian tubes, veins and other body lumens. A length of catheter 12 may depend on the location of the target tissue site within the body of a patient or may depend on the medical procedure for which catheter 12 is used. For example, if catheter 12 is a distal access catheter used to access vasculature in a brain of a patient from a femoral artery access point at the groin of the patient, then an elongated body of catheter 12 may have a working length of about 115 centimeters (cm) to about 145 cm or more, such as about 130 cm, although other lengths may be used (e.g., in the case of a radial access catheter). The distal portion may be about 5 cm to about 35 cm in length. The proximal portion may be about 90 cm to about 130 cm in length, depending on the length of the distal portion.

Pump 18 is configured to create a negative pressure (e.g., vacuum or suction) or otherwise induce fluid flow in inner lumen 26 of catheter 12, e.g., to draw fluid through inner lumen 26 and into discharge reservoir 24. Thus, pump 18 is configured to generate a pressure differential that causes fluid in inner lumen 26 to be drawn out of inner lumen 26 and towards pump 18, e.g., into discharge reservoir 24. For example, pump 18 may include a port configured to couple to aspiration tubing 22, such that the negative pressure created by fluid pump 18 may be applied to the port and through aspiration tubing 22 to a fluid pathway between aspiration tubing 22 and inner lumen 26 of catheter 12. In the example shown in FIG. 1, the fluid pathway further includes discharge reservoir 24, aspiration tubing 16, 20, and switch 14. In an example operation of pump 18, when distal opening 28 of catheter 12 is not blocked, pump 18 may draw fluid from inner lumen 26 of catheter 12 into discharge reservoir 24 through aspiration tubing 16, 20, and through switch 14. As another example, when distal opening 26 is partially or wholly blocked, pump 18 may draw fluid from catheter 12 at a reduced flow rate or, in some instances in which blockage is complete, draw no fluid at all. However, even when distal opening 26 is blocked, pump 18 may be configured to continue to create a vacuum on inner lumen 26 of catheter 12, e.g. via further evacuation of air from discharge reservoir 24.

Pump 18 may also be referred to as a fluid pump and can have any suitable configuration. For example, pump 18 (as well as pumps generally within the present disclosure) can include one or more of a positive displacement pump (e.g., a peristaltic pump, a rotary pump, a reciprocating pump, or a linear pump), a centrifugal pump, and the like. In some examples, pump 18 includes a motor driven pump, while in other examples, pump 18 can include a syringe configured to be controlled by control circuitry, and mechanical elements such as linear actuators, stepper motors, etc. As further examples, the pump 18 could comprise a water aspiration venturi or ejector jet.

In some examples, pump 18 may be configured for bi-directional operation. For example, pump 18 may be configured to create a negative pressure that draws fluid from inner lumen 26 of catheter 12 in a first flow direction and create a positive pressure that pumps fluid to catheter 12 and through inner lumen 26 of catheter 12 in a second, opposite flow direction. As an example of this bi-directional operation, an operator of aspiration system 10 may operate pump 18 to pump an aspiration/irrigating fluid, such as saline, from an aspiration fluid reservoir (not shown in FIG. 1) to flush and/or prime catheter 12 (e.g., an infusion state) and subsequently draw fluid from a site of distal opening 28 of catheter 12, such as saline and/or blood, into discharge reservoir 24.

In some examples, aspiration system 10 includes fluid flow switch 14 (also referred to herein as a fluid switch) to control fluid flow through aspiration system 10. Fluid switch 14 may be configured to start and stop fluid flow from catheter 12 toward pump 18 (or in the opposite direction). For example, fluid switch 14 may have an "open" position corresponding to flow of fluid through fluid switch 14 and a "closed" position corresponding to no flow of fluid through fluid switch 14. A variety of switching mechanisms may be used for fluid switch 14 including, but not limited to, valves, sliders, clamps and the like. In some example, fluid switch 14 may be configured for unaided operation by a clinician. For example, a mechanism of blocking fluid flow through fluid switch 14 may be directly operable by a mechanical force provided by the clinician. In other examples, system 10 does not include fluid switch 14.

Figure 2:
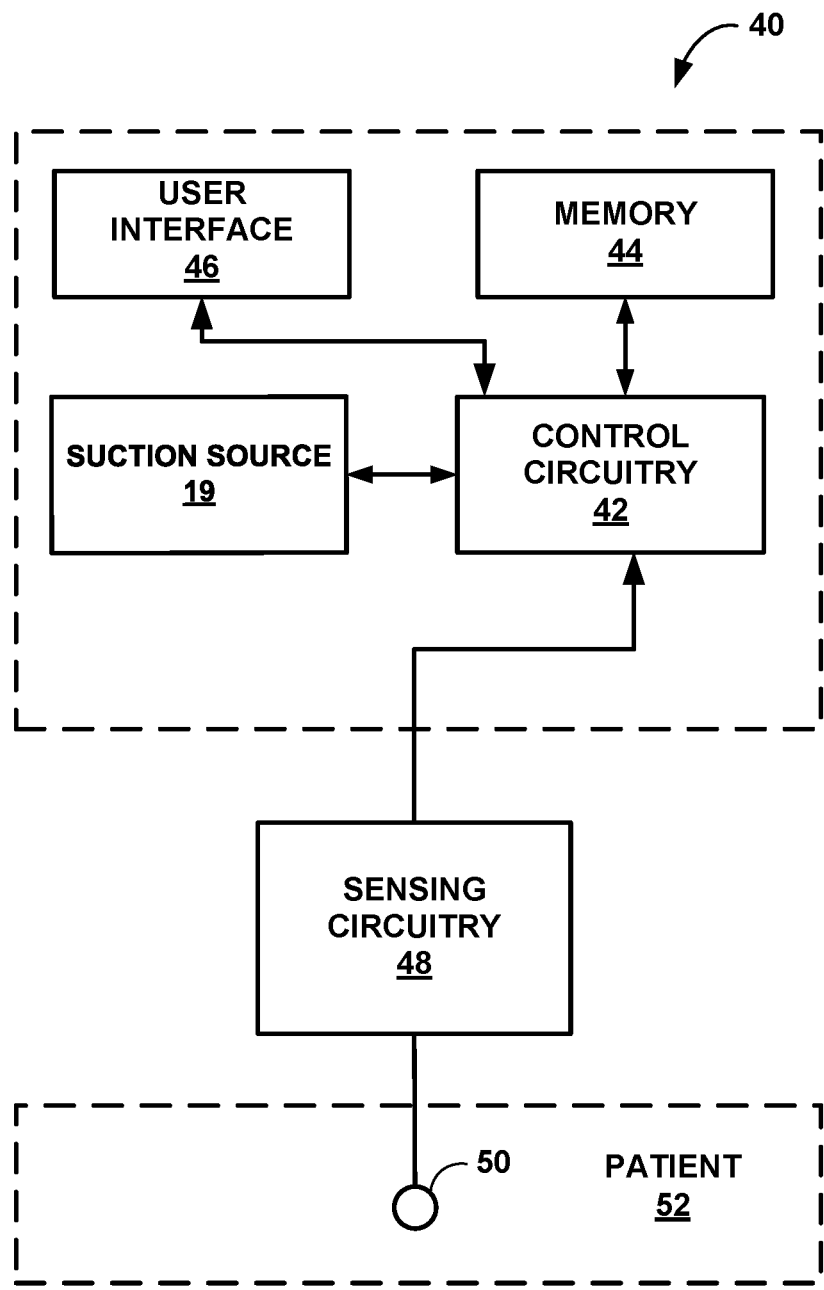
FIG. 2 is a schematic diagram illustrating another example aspiration system configured to control medical aspiration based on a cardiac cycle of a patient.

FIG. 2 is a block diagram of an example medical aspiration system 40, which is an example of medical aspiration system 10. Therefore, in some examples system 40 can be similar in structure and function to system 10, except as further discussed herein. Medical aspiration system 40 includes suction source 19 (which can comprise a pump (such as pump 18) and/or other component(s) as disclosed herein), control circuitry 42, a memory 44, a user interface 46, and sensing circuitry 48, which includes a sensor 50 configured to sense a physiological parameter of patient 52. Sensor 50 may also be referred to as a physiological parameter sensor. As discussed with reference to FIG. 1, suction source 19 is configured to be fluidically coupled to catheter 12 (FIG. 1) and apply a suction force to inner lumen 26 (FIG. 1) of catheter 12. Thus, although not shown in FIG. 2, aspiration system 40 can include one or more of aspiration tubing 16, 20, 22, fluid switch 14, and discharge reservoir 24 described with reference to FIG. 1.

Control circuitry 42 is configured to control a suction force applied by suction source 19 to catheter 12. For example, as described with reference to FIG. 4, control circuitry 42 can be configured to control a pulsator (e.g., valve) that modifies the suction force applied by suction source 19 to inner lumen 26 of catheter 12. In these examples, suction source 19 may apply a substantially continuous suction force (e.g., continuous or nearly continuous to the extent permitted by the hardware) to discharge reservoir 24, and the amount of this suction force that is transferred to inner lumen 26 may be adjusted by the pulsator (e.g., the position of the valve when implemented as such). As another example, as described with reference to FIG. 5, control circuitry 42 can be configured to more directly control an operation of pump 92/18 to vary the suction force applied by pump 92/18 to inner lumen 26, e.g. by controlling the motor speed, or stroke length, volume or frequency, or other operating parameters, of pump 92/18. Other techniques for modifying a suction force applied by suction source 19 to inner lumen 26 of catheter 12 can be used in other examples.

Control circuitry 42, as well as other processors, processing circuitry, controllers, control circuitry, and the like, described herein, may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, control circuitry 42 may include multiple components, such as any combination of one or more microprocessors, one or more DSPs, one or more ASICs, or one or more FPGAs, as well as other discrete or integrated logic circuitry, and/or analog circuitry.

Memory 44 may store program instructions, such as software, which may include one or more program modules, which are executable by control circuitry 42. When executed by control circuitry 42, such program instructions may cause control circuitry 42 to provide the functionality ascribed to control circuitry 42 herein. The program instructions may be embodied in software and/or firmware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some, but not all, examples, aspiration system 40 includes a user interface 46 configured to present information to a user and/or receive input from a user. For example, user interface 46 may include a display, an input device, and/or a speaker. In some examples, user interface 46 may include fewer or additional components. In some examples, a display of user interface 46 can present information indicative of a cardiac cycle of a patient, e.g., an EGM or an ECG, a heart sound phonocardiogram, a blood pressure signal, or PPG. In addition, in some examples, a clinician may interact with user interface 46 to control suction source 19, such as to start or stop suction source 19 from applying a suction force to catheter 12. The user interface 46 can include additional controls and displays, such as an indication of canister vacuum level, display and/or control of maximum vacuum limit, activation and/or deactivation of vacuum pulsation or variation, vacuum magnitude or amplitude (whether variable or constant), fault, and reset.

Sensing circuitry 48 is configured to receive signals (also referred to herein physiological signals) indicative of physiological parameters from sensor 50 and communicate the physiological signals to control circuitry 42. Sensing circuitry 48 and sensor 50 may include any sensing hardware configured to sense a physiological parameter of a patient, such as, but not limited to, one or more electrodes, optical receivers, pressure sensors, blood pressure cuffs, or the like. The sensed physiological signals may include signals indicative of a cardiac cycle of patient 52, such as, but not limited to, an electrocardiogram, an electrogram, a PPG, or a blood pressure signal. Thus, in some examples, sensing circuitry 48 and sensor 50 can be configured to include any suitable hardware configured to sense an electrical cardiac signal, blood pressure, or blood oxygen saturation (e.g., pulse oximetry) of patient 52. In some examples, sensing circuitry 48 can be integrated into, or some or all of its functions can be performed by, control circuitry 42.

In some examples, sensing circuitry 48 and/or control circuitry 42 may include signal processing circuitry configured to perform any suitable analog conditioning of the sensed physiological signals. For example, sensing circuitry 48 may communicate to control circuitry 42 an unaltered (e.g., raw) signal. Control circuitry 42 may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some examples, the conditioned analog signals may be processed by an analog-to-digital converter of control circuitry 42 or other component to convert the conditioned analog signals into digital signals. In some examples, control circuitry 42 may operate on the analog or digital form of the signals to separate out different components of the signals. In some examples, sensing circuitry 48 and/or control circuitry 42 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. Additionally or alternatively, sensing circuitry 48 may include signal processing circuitry to modify one or more raw signals and communicate to control circuitry 42 one or more modified signals.

In some examples, sensor 50 includes an ECG sensor, which includes electrodes with which sensing circuitry 48 may detect an electrical cardiac signal indicative of electrical activity of a heart of patient 52. In addition to or instead of the ECG sensor, in some examples, sensor 50 includes a blood oxygen saturation sensor with which sensing circuitry 48 can sense blood oxygen saturation levels of patient 52 and generate an oxygen saturation signal indicative of blood oxygen saturation within the venous, arterial, and/or capillary systems within a region of patient 52. For example, sensing circuitry 48 and sensor 50 may include a sensor configured to non-invasively generate a PPG signal. One example of such a sensor 50 may be one or more oximetry sensors (e.g., one or more pulse oximetry sensors) configured to be placed at one or multiple locations on patient 52, such as at a fingertip of patient 52, an earlobe of patient 52, and the like.

In addition to or instead of the ECG sensor and/or a blood oxygen saturation sensor, sensor 50 may include a blood pressure sensor with which sensing circuitry 48 can sense a blood pressure of patient 52 and generates a blood pressure signal indicative of the sensed blood pressure. For example, blood pressure sensor may include a continuous noninvasive blood pressure monitor and/or an arterial line configured to invasively (e.g. endoluminally) monitor blood pressure in an artery of patient 52. In some examples, the blood pressure signal may include at least a portion of a waveform of the arterial blood pressure.

In addition to or instead of the examples of sensors described above, sensor 50 can include an acoustic sensor configured to sense heart sounds with which control circuitry 42 or other control circuitry can determine a cardiac cycle of patient 52.

Sensing circuitry 48 and sensor 50 can be part of a device that includes control circuitry 42 or device separate from the device that includes control circuitry 42, such as another device co-located with the device that includes control circuitry 42 or remotely located relative to the device that includes control circuitry 42.

In some examples, control circuitry 42 operatively coupled to sensing circuitry 48 and is configured to control an operation of sensing circuitry 48 and sensor 50. For example, control circuitry 42 may be configured to provide timing control signals to coordinate operation of sensing circuitry 48 and sensor 50. In other examples, control circuitry 42 does not control the operation of sensing circuitry 48.

Figure 3:
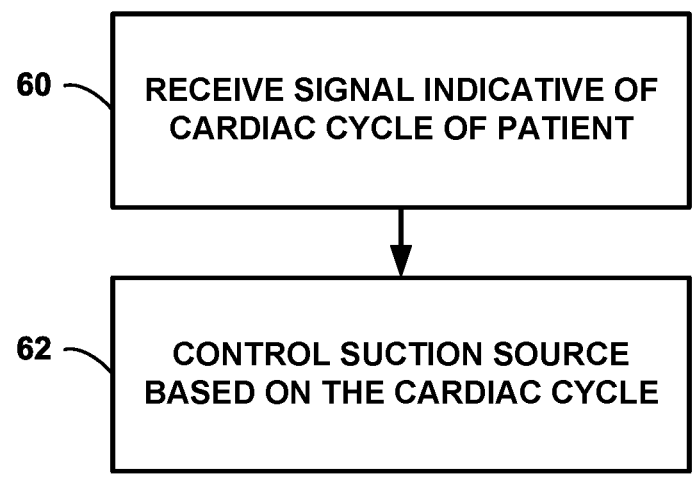
FIG. 3 is a flow diagram of an example technique for controlling a suction force applied by suction source to a catheter based on a cardiac cycle of a patient.

Control circuitry 42 is configured to receive one or more signals generated by sensing circuitry 48 and indicative of a cardiac cycle of patient 52, and control suction source 19 based on the signals. FIG. 3 is a flow diagram of an example method or technique for controlling a suction force applied by suction source 19 to catheter 12 based on a cardiac cycle of patient 52. While FIG. 3 is described with reference to systems 10, 40, and control circuitry 42, in other examples, the technique may be performed by another system, alone or in combination with systems 10, 40, including aspiration systems 70 and 90 shown in FIGS. 4 and 5, respectively.

As shown in FIG. 3, control circuitry 42 receives one or more signals indicative of a cardiac cycle of patient 52 (60). In some examples, the signals include physiological signal(s) generated by sensing circuitry 48 and/or sensor 50, and received from sensing circuitry 48. In addition to or instead of physiological signals, in some examples, the signals include an indication of a current part (e.g., phase) of a cardiac cycle patient 52 is in and can be received from another device that determines the current part of the cardiac cycle and transmits the determined part of the cardiac cycle to control circuitry 42. Thus, although not shown in FIG. 3, in some examples, aspiration system 40 includes communication circuitry configured to receive information from another device. The communication circuitry may be operable to communicate with external devices via one or more networks by transmitting and/or receiving network signals on the one or more networks. For example, control circuitry 42 may use the communication circuitry to transmit and/or receive radio signals on a radio network such as a cellular radio network, or on a satellite network. Examples of such communication circuitry include a network interface card (e.g. such as an Ethernet card), an optical transceiver, a radio frequency transceiver, or any other type of device that can send and/or receive information. Other examples of communication circuitry may include Near-Field Communications (NFC) units, Bluetooth® radios, short wave radios, cellular data radios, wireless network (e.g., Wi-Fi®) radios, as well as universal serial bus (USB) controllers.

Control circuitry 42 controls suction source 19 based on a cardiac cycle, as determined based on the received one or more signals (62). For example, control circuitry 42 can be configured to modify (or vary) the amount of suction force present at distal opening 28 of catheter 12 based on the part of cardiac cycle the heart of patient 52 is currently in as indicated by the or more signals generated by sensing circuitry 48. In some examples, control circuitry 42 is configured to control the suction force applied by suction source 19 based on the cardiac cycle by controlling suction source 19 (e.g., via an associated pulsator implemented as a valve, or fluid switch, or via other techniques of controlling suction source 19, as discussed herein) to apply a first suction force to inner lumen 26 of catheter 12 during a first part of a cardiac cycle (e.g., diastole) to generate a first suction force at distal catheter opening 28 and controlling suction source 19 to apply a second suction force to inner lumen 26 during another part of the cardiac cycle (e.g., systole) to generate a second suction force at distal catheter opening 28, the first suction force being different from the second suction force. In some examples, the first suction force is greater than the second suction force. In other examples, the first suction force is less than the suction force.

For example, the first suction force or the second suction force can be zero such that suction source 19 does not actively apply any suction force to catheter 12 during the respective first or second part of the cardiac cycle. However, in some cases, even if suction source 19 is not actively apply a suction force to catheter 12, there may be some residual vacuum in inner lumen 26 of catheter 12 due to its length and the time required for the pressure in inner lumen 26 to equalize with the environment external to catheter 12 at distal opening 28. Thus, even when suction source 19 is in an off-phase, in which suction source 19 is not actively operating to apply a suction force to catheter 12, a negative pressure in inner lumen 26 may still be observed. Thus, control circuitry 42 can be configured to cycle suction source 19 between an on-phase and an off-phase based on the cardiac cycle without causing the pressure differential between inner lumen 26 and the environment external to catheter 12 at distal opening 28 to be zero.

In some examples, control circuitry 42 is configured to control suction source 19 to apply a suction force to catheter 12, the applied suction force having a magnitude between a first suction force and a second suction force greater than the first suction force. The suction force range bounded by the first and second suction forces may be referred to as a suction force window. In some examples, the first suction force is 0 millimeters of mercury (mmHg). In some examples, control circuitry 42 controls suction source 19 to apply a greatest suction force of the suction force window to inner lumen 26 of catheter 12 during diastole. In these examples, control circuitry 42 may control suction source 19 to apply a lowest suction force of the suction force window to inner lumen 26 during systole or during another part of the cardiac cycle. Aligning a relatively highest (within the suction force window) suction force with diastole (e.g., between heart beats) may enable aspiration system 40 to apply a relatively greatest suction force to a thrombus when the blood vessel is relaxed and, therefore, may be less engaged with the thrombus.

In other examples, control circuitry 42 controls suction source 19 to apply a greatest suction force of the suction force window to inner lumen 26 of catheter 12 during systole. In these examples, control circuitry 42 may control suction source 19 to apply a lowest suction force of the suction force window to inner lumen 26 during diastole or during another part of the cardiac cycle. Aligning a relatively highest (within the suction force window) suction force with diastole may enable aspiration system 40 to establish a greater pressure differential between inner lumen 26 of catheter 12 and the blood vessel, as the blood pressure within the blood vessel may be greater during systole than during diastole.

During a cardiac cycle, control circuitry 42 may cycle suction source 19 between the highest and lowest vacuum pressures of the suction force window at a frequency of about 0.5 Hertz (Hz) to about 5 Hz (e.g., within 5%, 10%, or 20% of these values), or from about 0.5 Hz to about 10 Hz, or to about 20 Hz. In examples in which the lower bound of the suction force window is 0 mmHg, suction source 19 can be considered to be in an off-phase at the lower bound of the suction force window and in an on-phase at the higher bound of the suction force window.

Control circuitry 42 can control the suction force applied by suction source 19 to catheter 12 by modifying the operation (e.g., motor speed, or stroke length, volume or frequency) of pump 18 (where present) of suction source 19 and/or by operating, or controlling the state of, a pulsator of suction source 19, positioned between pump 18 (or discharge reservoir 24, where present) and catheter 12. The latter form of control may be implemented via the fluid switch of FIG. 2, or the valve 76 of FIG. 4.

In some examples, control circuitry 42 can be configured to control the suction force applied by suction source 19 based on the cardiac cycle (62) by controlling suction source 19 (e.g., via an associated pump, pulsator and/or discharge reservoir) to generate a minimum suction force at distal opening 28 of catheter 12 during a first part of the cardiac cycle and controlling suction source 19 to generate a maximum suction force at distal opening 28 during a second part of the cardiac cycle different from the first part. As an example, the second part can correspond to diastole or systole. As yet another example, the second part can correspond to a maximum ejection phase of the cardiac cycle (e.g., as indicated by an M-wave of a PQRST complex of an electrical cardiac signal).

Figure 4:
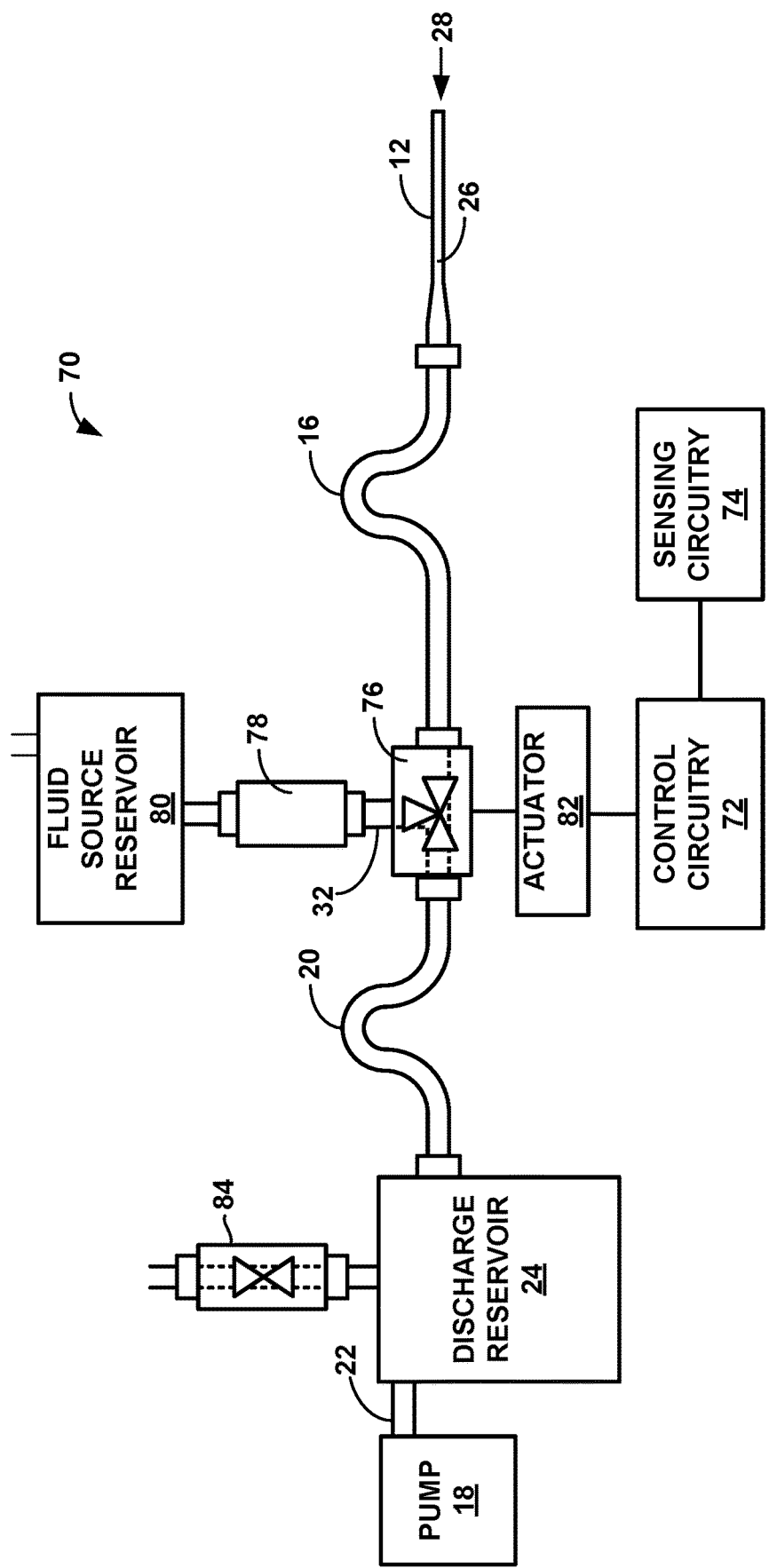
FIG. 4 is a schematic diagram illustrating another example aspiration system configured to control medical aspiration based on a cardiac cycle of a patient.

As discussed above, in some examples, control circuitry of an aspiration system can be configured to control an amount of suction force applied by a suction source to a catheter by controlling a pulsator that is configured to fluidically couple the suction source and the catheter. FIG. 4 is schematic diagram of an example of such an aspiration system 70, which is an example of aspiration systems 10, 40. Therefore, in some examples system 70 can be similar in structure and function to systems 10, 40, except as further discussed herein. Aspiration system 70 includes catheter 12, aspiration tubing 16, 20, 22, a suction source which can be implemented in part as a pump 18, and discharge reservoir 24 described with reference to FIG. 1. In addition, aspiration system 70 includes control circuitry 72 and sensing circuitry 74, which are examples of control circuitry 42 and sensing circuitry 48 described with reference to FIG. 2. Thus, although not shown in FIG. 4, in some examples, sensing circuitry 74 also includes a sensor configured to sense a physiological parameter indicative of a cardiac cycle of a patient. In addition, although not shown in FIG. 4, in some examples, aspiration system 70 includes fluid switch 14 (FIG. 1).

Aspiration system 70 can further comprise a pulsator (which can be implemented as a valve 76, or otherwise), a flow restrictor 78 and fluid source reservoir 80 connected to the valve 76 via tubing 32, and an actuator 82. In the example shown in FIG. 4, discharge reservoir 24 includes a relief valve 84 that controls the flow of gases into discharge reservoir 24 from an environment external to discharge reservoir 24. Control circuitry 72 or a clinician may adjust a setting of relief valve 84 in order to control or limit an amount of vacuum pressure developed within discharge reservoir 24 and/or passed through valve 76.

In the example shown in FIG. 4, control circuitry 72 is configured to control an amount of suction force applied by the suction source (e.g., pump 18) to inner lumen 26 of catheter 12 by at least controlling the pulsator (e.g., controlling a position of valve 76). In some examples of aspiration system 70, pump 18 is configured to apply a substantially continuous suction force (e.g., continuous or nearly continuous to the extent permitted by the hardware) to discharge reservoir 24, and the amount of this suction force that is transferred to inner lumen 26 of catheter 12 may be adjusted by the position of valve 76. In other examples, pump 18 is configured to apply pulsed aspiration, e.g., by alternating within a repeating cycle between "on" and "off" phases (during the latter of which no suction force, or reduced suction force is applied to tubing 22), rather than applying a substantially continuous suction force.

Valve 76 is movable between at least a first position and a second position. For example, valve 76 can be a two-position three-way valve, such as a three-way ball valve or another suitable valve, e.g., a pinch, poppet, diaphragm, butterfly, slide, or piston valve. Another suitable valve type is a 1-way or 2-way valve equipped with a relief vent (in which case the fluid source reservoir 80 can be omitted along with flow restrictor 78 and the connection to the valve 76). In the first position, valve 76 fluidically couples catheter 12 and fluid source reservoir 80, and catheter 12 and pump 18 are not fluidically coupled. Thus, in the first position of valve 76, pump 18 does not apply a suction force to inner lumen 26 of catheter 12 and does not draw fluid from inner lumen 26 into discharge reservoir 24. Fluid source reservoir 80 can store an incompressible fluid, such as saline; alternatively, it can be a source of compressible fluid such as a vent to ambient air via tubing 32. (In some examples, the fluid source reservoir 80 can be omitted along with flow restrictor 78 and the connection to the valve 76, which can take the form of a conventional two-way valve rather than the three-way valve depicted in FIG. 4.) Fluid source reservoir 80, when present, can be vented to an external environment. When valve 76 is in its first position, fluid source reservoir 80 is fluidically coupled to catheter 12, thereby relieving any negative pressure in catheter 12 or tubing 16, or otherwise allowing catheter 12 and tubing 16 to equalize with ambient pressure or a desired baseline pressure. In addition, when valve 76 is in its first position, pump 18 is configured to apply a negative pressure to tubing 22, which creates and/or maintains a negative pressure in discharge reservoir 24 Control circuitry 72 or a clinician can adjust a setting of flow restrictor 78 (when present) in order to adjust a rate of fluid flow from fluid source reservoir 80 to catheter 12 and/or tubing 16 when valve 76 is in its first position (and intermediary positions, as discussed in further detail below).

In the second position of valve 76, valve 76 fluidically couples pump 18 and catheter 12, and discharge reservoir 24 and fluid source reservoir 80 are not fluidically coupled to each other. Thus, in the second position of valve 76, pump 18 (via discharge reservoir 24) can apply a suction force to inner lumen 26 of catheter 12 and draw fluid from inner lumen 26 into discharge reservoir 24.

In some examples, valve 76 is also configured to assume positions between the first and second positions. In such intermediary positions, valve 76 is configured to permit some fluid flow from fluid source reservoir 80 to catheter 12 (the fluid flow being less than that observed when valve 76 is in its first position) and, at the same time, to permit some fluid flow from inner lumen 26 of catheter 12 to discharge reservoir 24 (the fluid flow being less than that observed when valve 76 is in its second position).

Control circuitry 72 is configured to control a position of valve 76 in order to control an amount of suction force applied by pump 18 to inner lumen 26 of catheter 12 using any suitable technique. In the example shown in FIG. 4, valve 76 is actuated between the first and second positions, including any intermediary positions, based on an amount of current applied (and/or signal(s) passed) to actuator 82. In some examples, actuator 82 can comprise a solenoid; in such a case, valve 76 can be referred to as a solenoid valve. Actuator 82 can alternatively comprise a linear or rotary actuator, servo, stepper motor, piezoelectric element(s), etc., or any other suitable component(s), or any combination of the foregoing. Control circuitry 72 can control an amount of current applied to (and/or pass signal(s) to) actuator 82 in order to modify a position of valve 76.

In some examples, control circuitry 72 is configured to receive information indicative of a cardiac cycle of a patient from sensing circuitry 74, and control (and/or actuate or initiate) a suction force applied by pump 18 to inner lumen 26 of catheter 12 based on the cardiac cycle by at least controlling a position of valve 76 based on the cardiac cycle. For example, control circuitry 72 can control whether (and/or the extent to which) valve 76 permits fluid communication between pump 18 and catheter 12 based on a part of a cardiac cycle the patient is in, as indicated by the received information. As an example, control circuitry 72 can position valve 76 in its first position in response to detecting the patient is in a first part of a cardiac cycle (e.g. diastole or systole) to turn aspiration off during the first part of the cardiac cycle, and position valve 76 in its second position in response to detecting the patient is a second part of the cardiac cycle (e.g., the other of diastole or systole) to turn aspiration on during the second part of the cardiac cycle.

In further examples, the pulsator employed in the system 70 of FIG. 4 can comprise one or more pinch valves. For example, a first pinch valve can be operatively coupled to tubing 20 and a second pinch valve can be operatively coupled to tubing 32. Such pinch valves can be operated to open and close tubing 20 and tubing 32 at appropriate times in accordance with the control techniques disclosed herein. In a first position of the pulsator, the first pinch valve is open and the second pinch valve is closed, and in a second position of the pulsator, the first pinch valve is closed and the second pinch valve is open. Tubing 32 can be connected to fluid source reservoir 80, with or without flow restrictor 78, or tubing 32 can terminate in an opening to ambient air. A check valve can be operatively coupled to tubing 32 on the side of the second pinch valve opposite the connection to tubing 20. The first and second pinch valves can be implemented with a common actuator forming a dual-acting pinch valve that alternatingly opens and closes the first and second pinch valves.

Figure 5:
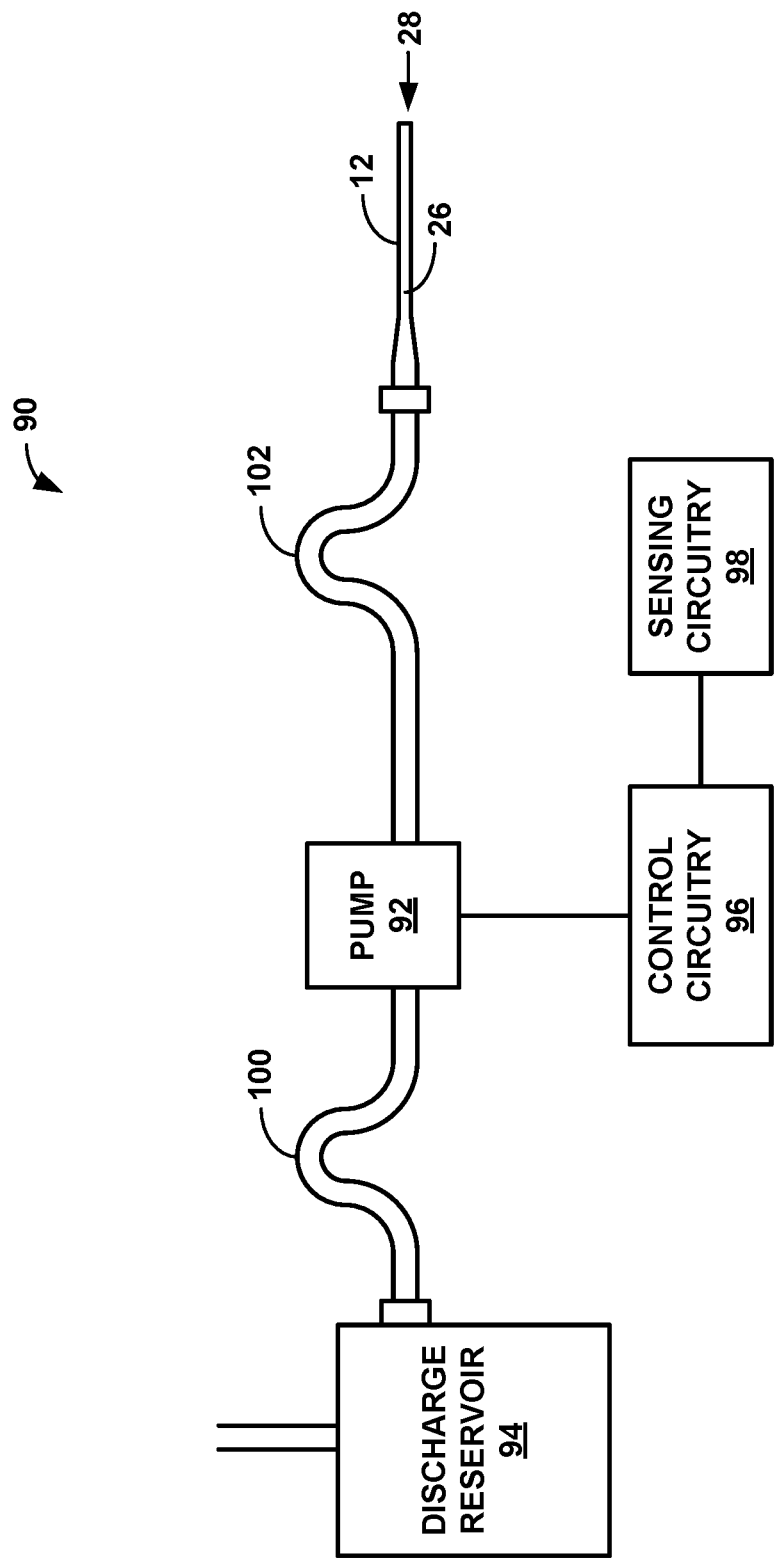
FIG. 5 is a schematic diagram illustrating another example aspiration system configured to control medical aspiration based on a cardiac cycle of a patient.

FIG. 5 is a schematic block diagram of another example aspiration system 90, which is another example of aspiration systems 10, 40. Therefore, in some examples system 90 can be similar in structure and function to system 10, except as further discussed herein. Aspiration system 90 includes catheter 12, pump 92, discharge reservoir 94, control circuitry 98, sensing circuitry 98, and aspiration tubing 102, 100. Pump 92 is fluidically coupled to aspiration tubing 102, which extends from a hub of catheter 12 to an inlet of pump 92 in the example shown in FIG. 5. In addition, pump 92 is fluidically coupled to discharge reservoir 94 via tubing 100, which extends from an outlet of pump 92 to discharge reservoir 94. Discharge reservoir 94 is similar to discharge reservoir 94 described with reference to FIG. 1, but rather than being positioned between a pump 18 and catheter 12 (along a fluid flow pathway between pump 18 and catheter 12), pump 92 is positioned between discharge reservoir 94 and catheter 12 (along a fluid flow pathway between reservoir 94 and catheter 12). In the example shown in FIG. 5, discharge reservoir 94 is configured to vent to an external environment.

Pump 92 is an example of pump 18 shown in FIG. 1. Control circuitry 96 and sensing circuitry 98 are examples of control circuitry 42 and sensing circuitry 48 described with reference to FIG. 2. Thus, although not shown in FIG. 4, in some examples, sensing circuitry 98 also includes a sensor configured to sense a physiological parameter indicative of a cardiac cycle of a patient. In addition, although not shown in FIG. 5, in some examples, aspiration system 90 includes fluid switch 14 (FIG. 1).

In the example shown in FIG. 5 and in contrast to the example aspiration system 70 shown in FIG. 4, control circuitry 96 is configured to control a suction force applied by pump 92 to catheter 12 by directly controlling an operation of pump 92, in addition to or instead of controlling the position of valve 76 (FIG. 4). Pump 92 can include, for example, a peristaltic pump or a diaphragm pump. Control circuitry 96 can control an operation of pump 92 based on a cardiac cycle using any suitable technique. In some examples, control circuitry 96 operates pump 92 in a repeating cycle having an "on" phase, in which pump 92 is configured to apply a preset suction force to inner lumen 26, followed by an "off" phase, in which pump 92 does not actively apply a preset suction force to inner lumen 26. For example, control circuitry 96 can be configured to select whether pump 92 is in an on-phase or an off-phase based on a current part of a cardiac cycle of the patient, as indicated by the information received from sensing circuitry 98. As an example, control circuitry 96 can control the timing and/or duration of the on-phase and off-phase of pump 92 such that a greatest suction force at distal opening 28 of catheter 12 (e.g., a maximum suction force of a predetermined suction force window used for a particular aspiration procedure) is observed during diastole or systole.

The techniques described in this disclosure, including those attributed to control circuitry 42, 72, and 96, and sensing circuitry 48, 74, and 98, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example. In addition, analog circuits, components and circuit elements may be employed to construct one, some or all of the control circuitry 42, 72, and 96, and sensing circuitry 48, 74, and 98, instead of or in addition to the partially or wholly digital hardware and/or software described herein. Accordingly, analog or digital hardware may be employed, or a combination of the two. Whether implemented in digital or analog form, or in a combination of the two, the control circuitry 42, 72, and 96 can comprise a timing circuit configured to command the application of a suction force (via, e.g., command of the pulsator) in synchrony with the patient's cardiac cycle. This can be done by sending the command in response to sensing a desired feature of the cardiac cycle (or a simple heart beat), incorporating if needed an applicable time lag.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

Various examples of the disclosure have been described. Any combination of the described systems, operations, or functions is contemplated. These and other examples are within the scope of the following claims.

What is claimed is:

1. A medical aspiration system comprising:
a suction source configured to apply a suction force to a catheter to remove a thrombus from vasculature of a patient using the catheter; and
control circuitry configured to control the suction force applied by the suction source to the catheter based on a cardiac cycle of the patient to vary the suction force present at a distal opening of the catheter to facilitate aspiration of the thrombus from the vasculature.

2. The medical aspiration system of claim 1, wherein the control circuitry is configured to control the suction force applied by the suction source based on the cardiac cycle by at least controlling the suction source to apply a first suction force during diastole and controlling the suction source to apply a second suction force during systole, the first suction force being different from the second suction force.

3. The medical aspiration system of claim 1, further comprising sensing circuitry configured to generate a signal indicative of the cardiac cycle of the patient, wherein the control circuitry is configured to receive the signal from the sensing circuitry and control the suction force applied to the catheter based on the signal.

4. The medical aspiration system of claim 3, wherein the signal comprises at least one of an electrocardiogram, an electrogram, a photoplethysmogram, or a blood pressure signal.

5. The medical aspiration system of claim 1, further comprising the catheter fluidically coupled to the suction source, wherein the catheter comprises a flexible catheter body configured to be navigated through the vasculature of the patient.

6. The medical aspiration system of claim 1, wherein the control circuitry is configured to control the suction force applied by the suction source to the catheter based on the cardiac cycle by at least cycling the suction source between an on-phase and an off-phase.

7. The medical aspiration system of claim 1, wherein the control circuitry is configured to synchronize the application of suction force with the cardiac cycle.

8. The medical aspiration system of claim 1, wherein the control circuitry is configured to synchronize the application of suction force with one portion of the cardiac cycle, and the application of reduced suction force or no suction force with another portion of the cardiac cycle.

9. The medical aspiration system of claim 1, wherein the control circuitry is configured to synchronize the application of suction force with one portion of the cardiac cycle, and apply reduced suction force or no suction force during the remainder of the cardiac cycle.

10. The medical aspiration system of claim 1, wherein the suction source comprises a pulsator, and the control circuitry is configured to control the suction force applied by the suction source by controlling the pulsator.

11. The medical aspiration system of claim 10, wherein the pulsator comprises a valve.

12. A method comprising:
receiving, in a medical aspiration system, a signal indicative of a cardiac cycle of a patient; and
controlling a suction force applied by a suction source of the medical aspiration system to a catheter to remove a thrombus from vasculature of the patient based on the signal indicative of the cardiac cycle to vary the suction force present at a distal opening of the catheter to facilitate aspiration of the thrombus from the vasculature.

13. A medical aspiration system comprising:
a suction source configured to apply a suction force to a catheter to remove fluid from the catheter, wherein the catheter is configured to be navigated to a target tissue site in vasculature of a patient; and
control circuitry configured to receive a signal indicative of a cardiac cycle of the patient from sensing circuitry, determine a current part of the cardiac cycle of the patient based on the signal, and control the suction force applied by the suction source to the catheter based on the determined current part of the cardiac cycle to facilitate aspiration of a thrombus from the vasculature.

14. The medical aspiration system of claim 13, wherein the control circuitry is configured to control the suction force applied by the suction source by at least:
in response to determining the current part of the cardiac cycle is diastole, controlling the suction source to apply a first suction force, and
in response to determining the current part of the cardiac cycle is systole, controlling the suction source to apply a second suction force during systole, the first suction force being different from the second suction force.

15. The medical aspiration system of claim 13, wherein the control circuitry is configured to control the suction force applied by the suction source based on the determined current part of the cardiac cycle by at least controlling the suction source to generate a first suction force at a distal opening of a catheter during a first part of the cardiac cycle and to generate a second suction force at the distal opening of the catheter during a second part of the cardiac cycle different from the first part, the second suction force being greater than the first suction force.

16. The medical aspiration system of claim 13, further comprising sensing circuitry configured to generate a signal indicative of the cardiac cycle of the patient, wherein the control circuitry is configured to receive the signal from the sensing circuitry and determine the current part of the cardiac cycle based on the signal.

17. The medical aspiration system of claim 16, wherein the signal comprises at least one of an electrocardiogram, an electrogram, a photoplethysmogram, or a blood pressure signal.

18. The medical aspiration system of claim 13, further comprising the catheter fluidically coupled to the suction source, wherein the catheter comprises a flexible catheter body configured to be navigated through the vasculature of the patient.

19. The medical aspiration system of claim 13, wherein the control circuitry is configured to control the suction force applied by the suction source to the catheter based on the determined current part of the cardiac cycle by at least cycling the suction source between an on-phase and an off-phase.

20. The medical aspiration system of claim 13, wherein the control circuitry is configured to synchronize the application of suction force with the cardiac cycle.

21. The medical aspiration system of claim 13, wherein the control circuitry is configured to synchronize the application of suction force with one portion of the cardiac cycle, and the application of reduced suction force or no suction force with another portion of the cardiac cycle.

22. The medical aspiration system of claim 13, wherein the suction source comprises a pulsator, and the control circuitry is configured to control the suction force applied by the suction source by controlling the pulsator.

23. The medical aspiration system of claim 1, wherein the control circuitry is configured to control the suction force based on the cardiac cycle to create sufficient suction force at the distal opening of the catheter to engage the thrombus with the distal opening of the catheter.

24. The medical aspiration system of claim 1, wherein the control circuitry is configured to control the suction force based on the cardiac cycle by at least controlling the suction force to time application of a relatively high suction force to the catheter with a predetermined part of the cardiac cycle.

* * * * *